(12) United States Patent
Williams et al.

(10) Patent No.: US 8,481,012 B2
(45) Date of Patent: Jul. 9, 2013

(54) ANTIPERSPIRANT EMULSION PRODUCTS AND PROCESSES FOR MAKING ANTIPERSPIRANT EMULSION PRODUCTS

(75) Inventors: Berea A. R. Williams, Scottsdale, AZ (US); Thomas Doering, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 280 days.

(21) Appl. No.: 12/977,331

(22) Filed: Dec. 23, 2010

(65) Prior Publication Data

US 2012/0160365 A1   Jun. 28, 2012

(51) Int. Cl.
*A61K 8/00* (2006.01)
*A61K 8/18* (2006.01)
*A61Q 15/00* (2006.01)

(52) U.S. Cl.
USPC .......................................................... 424/65

(58) Field of Classification Search
USPC .......................................................... 424/65
See application file for complete search history.

(56) References Cited

U.S. PATENT DOCUMENTS

| | | | |
|---|---|---|---|
| D449,405 S | 10/2001 | Gersten et al. | |
| D456,560 S | 4/2002 | Gersten et al. | |
| D456,923 S | 5/2002 | Koenig | |
| D456,941 S | 5/2002 | Gersten et al. | |
| D457,263 S | 5/2002 | Gersten et al. | |
| D457,264 S | 5/2002 | Gersten et al. | |
| D474,963 S | 5/2003 | Gersten et al. | |
| D474,964 S | 5/2003 | Gersten et al. | |
| D478,186 S | 8/2003 | Gersten et al. | |
| 6,723,269 B2 | 4/2004 | Grosz et al. | |
| 6,776,981 B2 | 8/2004 | Elliott et al. | |
| 6,838,032 B2 | 1/2005 | Grosz et al. | |
| 6,936,242 B2 | 8/2005 | Elliott et al. | |
| 2002/0155077 A1 | 10/2002 | Galante et al. | |
| 2004/0241122 A1 | 12/2004 | Popoff et al. | |
| 2009/0304616 A1 | 12/2009 | Banowski et al. | |
| 2011/0038822 A1 | 2/2011 | Phipps et al. | |

FOREIGN PATENT DOCUMENTS

WO   2009077453 A1   6/2009

OTHER PUBLICATIONS

PCT International Search Report (PCT/US2011/067118) dated Sep. 26, 2012.

*Primary Examiner* — Daniel Sullivan
*Assistant Examiner* — Trevor Love
(74) *Attorney, Agent, or Firm* — David K. Benson

(57) ABSTRACT

Antiperspirant emulsion products and processes for forming antiperspirant emulsion products are provided. One process for making an antiperspirant emulsion product comprises the steps of heating and mixing water and an active antiperspirant compound to a first temperature to form a water phase. A hydrophobic carrier, a structurant, and cetyl PEG/PPG-10/1 dimethicone are heated and mixed to a second temperature that is greater than the first temperature to melt the structurant and form an oil phase. The oil phase is cooled and mixed to a third temperature. The water phase is gradually added to the oil phase to form an antiperspirant emulsion so that the water phase is present in an amount of from about 54 to about 89 wt. % and the oil phase is present in an amount of from about 11 to about 46 wt. % of the antiperspirant emulsion.

12 Claims, 1 Drawing Sheet

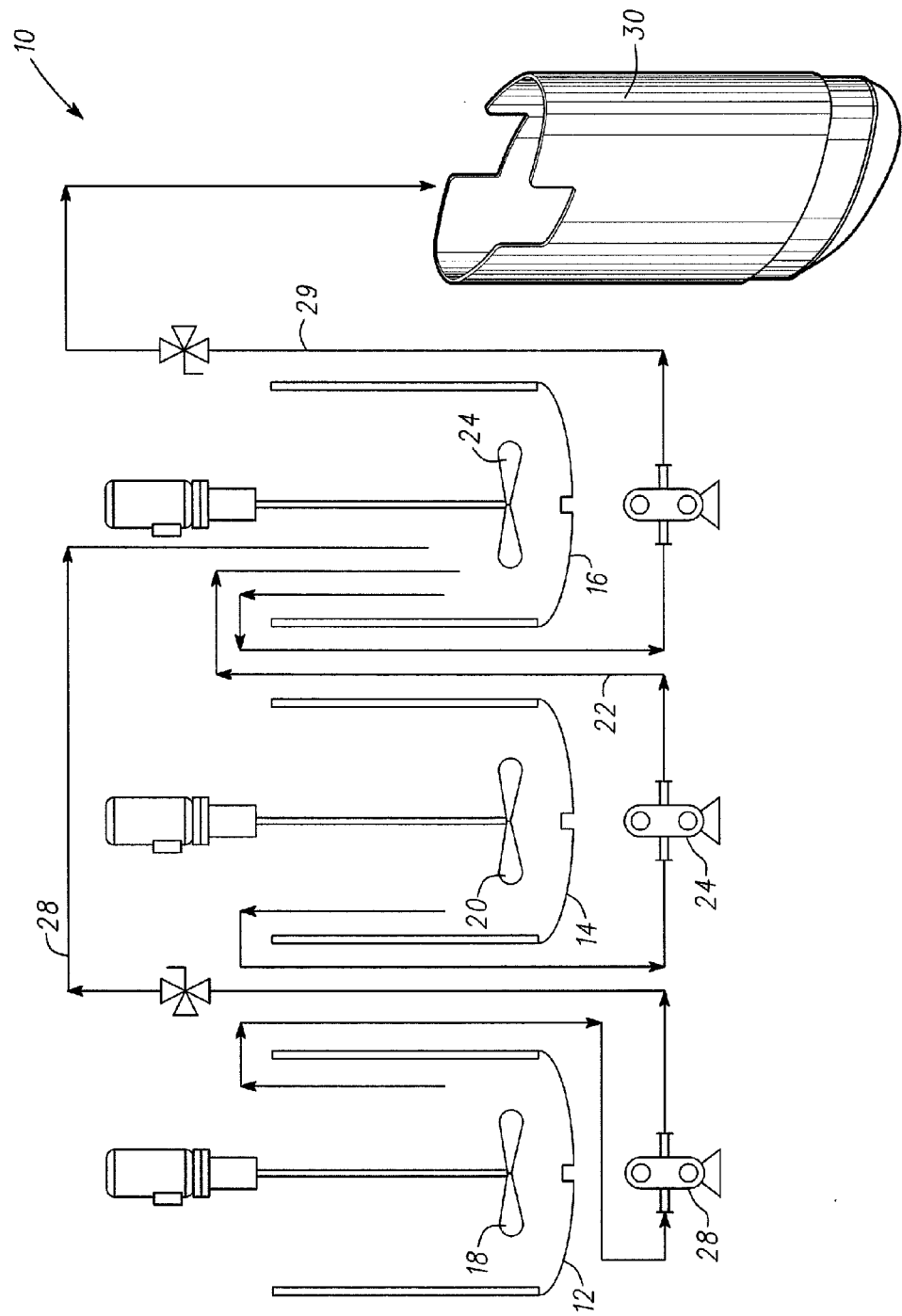

ANTIPERSPIRANT EMULSION PRODUCTS AND PROCESSES FOR MAKING ANTIPERSPIRANT EMULSION PRODUCTS

FIELD OF THE INVENTION

The present invention generally relates to antiperspirant products and processes for making the antiperspirant products, and more particularly relates to antiperspirant emulsion products having different antiperspirant stick hardness that exhibit antiperspirant efficacy with the enhanced feel of a deodorant and processes for making the antiperspirant emulsion products.

BACKGROUND OF THE INVENTION

Antiperspirants and deodorants are popular personal care products used to prevent or eliminate perspiration and body odor caused by perspiration. Antiperspirants typically prevent the secretion of perspiration by blocking or plugging sweat-secreting glands, such as those located at the underarms. Deodorants counteract or mask the unwanted odors caused by bacterial flora in secreted sweat.

Antiperspirant sticks are desired by a large majority of the population because of the presence of antiperspirant active compounds that block or prevent the secretion of perspiration and the accompanying odors thereof and because of their ease of application. The antiperspirant product is applied to the skin by swiping or rubbing the stick across the skin, typically of the underarm. However, antiperspirant users often are disappointed in the chalky, brittle, and/or crumbly application of the stick across the skin. Deodorants, on the other hand, typically provide a better "glide" and an evenness of the coverage of the deodorant product across the underarm skin. The term "glide" typically is used to denote the friction between the antiperspirant and/or deodorant product and the skin. The smoother the glide, or the less friction between the product and the skin, the more desirable the product to users. While deodorants typically exhibit smoother glide than antiperspirant sticks, they do not prevent or minimize the secretion of perspiration as do antiperspirants because they do not contain active antiperspirant compounds. Active antiperspirant compounds generally cannot be added to deodorants because the alkalinity of the deodorants cause the antiperspirant compounds, typically acidic, to precipitate or settle out of deodorants. Thus, there is a need for antiperspirant products that exhibit antiperspirant efficacy with the feel of deodorants.

Men typically desire harder stick antiperspirant products with lower payout, while women typically desire softer stick antiperspirant products with higher payout. Payout is the amount of antiperspirant product, usually measured in grams weight, transferred per swipe during application. In general, men prefer to apply antiperspirant products by using more pressure and multiple swipes while women prefer to apply antiperspirant products using less pressure and fewer swipes, e.g., a single swipe. Unfortunately, many antiperspirant products when applied leave behind an undesirable color residue that is typically white. By applying more pressure to harder stick antiperspirant products and using multiple swipes during application, the amount of color residue left behind can substantially increased. Alternatively, by using softer stick antiperspirant products that have higher payout, the amount of color residue left behind can also be substantial. Thus, there is a need for both relatively hard and soft stick antiperspirant products that leave behind less color residue and provide an evenness of the coverage.

Accordingly, it is desirable to provide antiperspirant products that exhibit antiperspirant efficacy with the application characteristic and feel of deodorants. It is also desirable to provide relatively hard and soft stick antiperspirant products with corresponding relatively low and high payouts that leave behind less color residue and provide an evenness of the coverage. In addition, it is desirable to provide processes for making such antiperspirant products. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

In accordance with an exemplary embodiment, a process for making an antiperspirant emulsion product is provided. The process comprises the steps of heating and mixing water and an active antiperspirant compound to a first temperature to form a water phase. A hydrophobic carrier, a structurant, and cetyl PEG/PPG-10/1 dimethicone are heated and mixed to a second temperature that is greater than the first temperature to melt the structurant and form an oil phase. The oil phase is cooled and mixed to a third temperature. The water phase is gradually added to the oil phase to form an antiperspirant emulsion so that the water phase is present in an amount of from about 54 to about 89 wt. % and the oil phase is present in an amount of from about 11 to about 46 wt. % of the antiperspirant emulsion.

In accordance with another exemplary embodiment, an antiperspirant emulsion product is provided. The antiperspirant emulsion product comprises a water-in-oil emulsion having a water phase and an oil phase. The water phase comprises an active antiperspirant compound and water and the oil phase comprises a hydrophobic carrier, a structurant, and cetyl PEG/PPG-10/1 dimethicone. The water phase is present in an amount of from about 54 to about 89 wt. % and the oil phase is present in an amount of from about 11 to about 46 wt. % of the antiperspirant emulsion product.

In accordance with another exemplary embodiment, a process for making an antiperspirant emulsion product is provided. The process comprises the steps of heating to about 80 to about 90° C. and mixing water and an active antiperspirant compound to form a precursor harder stick and lower payout water phase or heating to about 70 to about 79° C. and mixing water and the active antiperspirant compound to form a precursor softer stick and higher payout water phase. A hydrophobic carrier, a structurant, and cetyl PEG/PPG-10/1 dimethicone are heated to about 90 to about 95° C. and mixed to form an oil phase. The oil phase is cooled to about 80 to about 90° C. to form a precursor harder stick and lower payout oil phase or the oil phase is cooled to about 70 to about 79° C. to form a precursor softer stick and higher payout oil phase. The precursor harder stick and lower payout water phase is combined with the precursor harder stick and lower payout oil phase to form a harder stick and lower payout antiperspirant emulsion product or the precursor softer stick and higher payout water phase is combined with the softer stick and higher payout oil phase to form a softer stick and higher payout antiperspirant emulsion product.

BRIEF DESCRIPTION OF THE DRAWINGS

The present invention will hereinafter be described in conjunction with the following drawing figures, wherein like numerals denote like elements, and wherein:

FIG. 1 schematically illustrates an emulsion processing system for making an antiperspirant emulsion product in accordance with an exemplary embodiment.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The various embodiments contemplated herein relate to antiperspirant emulsion products with antiperspirant efficacy that exhibit improved skin feel. The various embodiments of the antiperspirant emulsion products comprise cetyl PEG/PPG-10/1 dimethicone as an emulsifier. It has been unexpectedly found that the use of cetyl PEG/PPG-10/1 dimethicone as an emulsifier in an antiperspirant product causes the antiperspirant product to exhibit skin feel characteristics that are typical of deodorant products. For example, with cetyl PEG/PPG-10/1 dimethicone, the antiperspirant emulsion products glide onto skin with less friction, that is, in a smoother manner, than conventional antiperspirants while still maintaining a solid consistency for easy application. The various embodiments of the antiperspirant emulsion products also comprise a unique combination of structurants that result in less color residue on the skin. Further, the various embodiments contemplated herein relate to unique processes for making the antiperspirant emulsion products that result in either relatively hard or soft antiperspirant sticks with corresponding relatively low or high payouts.

In this regard, in one exemplary embodiment of the present invention, the antiperspirant emulsion product, hereinafter referred to as the antiperspirant product, is a water-in-oil emulsion comprising a water phase mixed with an oil phase. Preferably, the antiperspirant product comprises a water phase in an amount of about 54 to about 89 weight percent (wt. %) of the total antiperspirant product and an oil phase in an amount of about 11 to about 46 wt. % of the total antiperspirant product. The antiperspirant product preferably has a non-flowing, solid composition that can be rubbed or wiped across the skin, particularly the underarm.

In one exemplary embodiment, the antiperspirant product has a stick hardness of from about 0.99 to about 2.7 newtons (N), and more preferably of from about 1.1 to about 2.7 N, and a payout of about 0.75 to about 1.25 g per 3 swipes. In this example, the stick hardness was determined using a Stable Micro System TA.XT express Texture Analyzer, which is manufactured by Stable Micro Systems LTD. located in the United Kingdom, using the following conditions and procedure: Trigger Force=5 g, Test Speed 1 mm/sec, Distance=5 mm, and a TA 17 30° cone positioned on a probe was moved down into the antiperspirant product until the desired trigger force was detected, and then the probe was moved down about 5 mm at about 1 mm/sec into the antiperspirant product where the resulting force was displayed on the instrument and recorded for the stick hardness. The payout was determined using the following procedure: the top dome of the antiperspirant product was cut off and the remaining stick was weighed, the base of the antiperspirant stick was then taped to the bottom of a 250 mL beaker, a 1 kg weight was placed into the beaker, a paper towel was secured to a heating plate set at about 50° C., the antiperspirant product was then placed onto the paper towel, the antiperspirant product was moved across the paper towel over an area of about 5 cm by about 20 cm at a fixed rate for a total of 3 swipes (down and back), the antiperspirant stick without the beaker was then weighed, the final weight was subtracted from the initial weight for the total payout, and this procedure was repeated 3 times and averaged for the final total payout. As such, the antiperspirant product has a relatively high stick hardness and low payout, which is typically more desirable by men. In another exemplary embodiment, the antiperspirant product has a stick hardness of about 0.29 to about 0.98 N, and more preferably of about 0.29 to about 0.9 N, and a payout of about 2 g or greater per 3 swipes. As such, the antiperspirant product has a relatively soft stick hardness and high payout, which is typically more desirable by women. Preferably, the solid composition is substantially snow white in color, thus suggesting a clean and/or sterile nature.

The water phase of the antiperspirant product comprises a water-soluble active antiperspirant compound. Active antiperspirant compounds contain at least one active ingredient, typically metal salts, that are thought to reduce sweating by diffusing through the sweat ducts of eccrine glands and hydrolyzing in the sweat ducts, where they combine with proteins to form an amorphous metal hydroxide agglomerate, plugging the sweat ducts so sweat can not diffuse to the skin surface. Some active antiperspirant compounds that may be used in the antiperspirant product include astringent metallic salts, especially inorganic and organic salts of aluminum, zirconium, and zinc, as well as mixtures thereof. Particularly preferred are aluminum-containing and/or zirconium-containing salts or materials, such as aluminum halides, aluminum chlorohydrates, aluminum hydroxyhalides, zirconyl oxyhalides, zirconyl hydroxyhalides, and mixtures thereof. Exemplary aluminum salts include those having the general formula $Al_2(OH)_a Cl_b \times (H_2O)$, wherein a is from 2 to about 5; a and b total to about 6; x is from 1 to about 6; and wherein a, b, and x may have non-integer values. Exemplary zirconium salts include those having the general formula $ZrO(OH)_{2-a} Cl_a x(H_2O)$, wherein a is from about 1.5 to about 1.87, x is from about 1 to about 7, and wherein a and x may both have non-integer values. Particularly preferred zirconium salts are those complexes that additionally contain aluminum and glycine, commonly known as ZAG complexes. These ZAG complexes contain aluminum chlorohydroxide and zironyl hyroxy chloride conforming to the above-described formulas. Examples of active antiperspirant compounds suitable for use in the various embodiments contemplated herein include aluminum dichlorohydrate, aluminum zirconium octachlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum zirconium trichlorohydrate, aluminum zirconium tetrachlorohydrate, aluminum zirconium pentachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, zirconium chlorohydrate, aluminum chloride, aluminum sulfate buffered, aluminum chlorohydrate, aluminum chlorohydrex, aluminum chlorohydrex PG, aluminum sesquichlorohydrex PG, aluminum zirconium tetrachlorohydrex PEG, aluminum zirconium tetrachlorohydrex PG and the like, and mixtures thereof. In a preferred embodiment, the antiperspirant compound is aluminum zirconium octachlorohydrex complex with glycine and calcium chloride. In another embodiment, the antiperspirant product comprises an active antiperspirant compound present in the amount of 12 to about 20 weight percent (USP). As used herein, weight percent (USP) or wt. % (USP) of an antiperspirant salt is calculated as anhydrous weight percent in accordance with the U.S.P. method, as is known in the art. This calculation excludes any bound water.

In an exemplary embodiment, the water phase also comprises at least one water soluble carrier/solubilizer present in a sufficient amount to solubilize or disperse the water phase ingredients of the antiperspirant product. Such carriers/solubilizers suitable for use in the antiperspirant product include, but are not limited to, propylene glycol, glycerol, dipropyl glycol, ethylene glycol, butylene glycol, propylene carbonate, dimethyl isosorbide, hexylene glycol, ethanol, n-butyl alcohol, n-propyl alcohol, isopropyl alcohol, and the like. In a preferred embodiment, the water phase comprises propylene glycol and, in a more preferred embodiment, the water phase comprises propylene glycol in an amount of about 10 to about 15 wt. % of the total antiperspirant product. In addition to the carrier/solubilizer, the antiperspirant product comprises water. In an exemplary embodiment, the water phase comprises water in an amount of 30 to about 50 wt. % of the total antiperspirant product. Preferably, the water evaporates from the antiperspirant product upon application of the antiperspirant product to the skin, providing a cooling sensation to the skin.

The water phase also may comprise optional ingredients that serve a particular purpose. In one exemplary embodiment, the water phase comprises an activator for the active antiperspirant compound. In a preferred embodiment, the water phase comprises calcium chloride, and in a more preferred embodiment, comprises calcium chloride in an amount of about 2 to about 4 wt. % of the total antiperspirant product.

The oil phase of the antiperspirant product comprises an emulsifier of cetyl PEG/PPG-10/1 dimethicone, in accordance with an exemplary embodiment. Cetyl PEG/PPG-10/1 dimethicone is a copolymer of cetyl dimethicone and an alkoxylated derivative of dimethicone containing an average of 10 moles of ethylene oxide and 1 mole of propylene oxide. As noted above, the use of cetyl PEG/PPG-10/1 dimethicone as an emulsifier in the antiperspirant product causes the antiperspirant product to exhibit skin feel characteristics that are typical of deodorant products. For example, with cetyl PEG/PPG-10/1 dimethicone, the antiperspirant products glide onto the skin with less friction while still maintaining a solid consistency for easy application. In addition, when applied, the antiperspirant products are moister than typical antiperspirants and thus give the skin a moister and softer feel. In a preferred embodiment, the oil phase comprises cetyl PEG/PPG-10/1 dimethicone in an amount of about 1 to about 3 wt. % of the total antiperspirant product.

Further included in the oil phase of the antiperspirant product is at least one structurant and/or gellant (hereinafter referred collectively as structurant) that facilitates the solid consistency of the antiperspirant stick product. Naturally-occurring or synthetic waxy materials or combinations thereof can be used as such structurants. Examples of these waxy materials include those fatty alcohols that are solid at room temperature and hydrocarbon waxes or silicone waxes. Such materials are widely available, and by suitable selection of the materials themselves and their concentrations in the formulation, it is possible to obtain either a softer solid stick or a firmer solid stick. In a preferred embodiment, the oil phase comprises a high molecular weight (MW) polyethylene. As used herein, the term "high molecular weight polyethylene" or "high MW polyethylene" means polyethylene having a molecular weight of 200 to 5000 daltons (Da). In a more preferred embodiment, the oil phase comprises high MW polyethylene having a molecular weight of about 500 Da. In another preferred embodiment, the oil phase comprises high MW polyethylene in an amount of about 4 to about 12 wt. % of the total antiperspirant product.

In this regard, polyethylene can be used in smaller amounts as a structurant in the antiperspirant products than other structurants, such as stearyl alcohol, that can exhibit undesirable properties in the antiperspirant product. Stearyl alcohol is commonly used as a structurant in solid stick underarm products. However, stearyl alcohol has a tendency to leave visible white color deposits, e.g., color residue, on the skin, and the deposits can also transfer onto clothing when the clothing comes into contact with the skin. Accordingly, in another preferred embodiment, the oil phase comprises substantially no stearyl alcohol. The term "substantially no stearyl alcohol" as used herein means no stearyl alcohol or stearyl alcohol in an amount that is sufficiently small so that it would not cause visible white color residue to deposit on skin and/or clothing after application of the antiperspirant product to the skin.

In accordance with another exemplary embodiment, when high MW polyethylene is used in the oil phase as a structurant, the oil phase also comprises at least one low MW synthetic wax. In addition to facilitating the high MW polyethylene by serving a structurant function, the low MW synthetic wax also improves the manufacturing processes of the antiperspirant products. Generally, polyethylene has a relatively high melting point of up to about 90 or about 100° C. or greater, and thus, the oil phase of the antiperspirant product must be heated to this high melting point to melt the polyethylene. The presence of an effective amount of low MW synthetic wax (synthetic wax having a molecular weight in the range of 1200-2900 Da) modifies the high MW polyethylene, lowering the melting point of the polyethylene preferably to about 90 to about 95° C. In an exemplary embodiment, the low MW synthetic wax is present in the oil phase in an amount of about 0 to about 3 wt. % of the total antiperspirant product. In another exemplary embodiment, the low MW synthetic wax has a molecular weight of about 1800. In addition to improving hardness of the antiperspirant stick product, the low MW synthetic wax reduces syneresis and tackiness and also has a high refractive index (R.I.) that minimizes and/or prevents a color residue on the skin by masking the antiperspirant metallic salt(s) that stays upon the skin upon evaporation of the carrier(s). As used herein, the term "high refractive index" means an refractive index no less than about 1.4. While the use of low MW synthetic wax to lower the melting point of high MW polyethylene is described herein in the context of an antiperspirant product comprising cetyl PEG/PPG-10/1 dimethicone as an emulsifier, it will be appreciated that low MW synthetic wax can be used to lower the melting point of high MW polyethylene in an antiperspirant emulsion product containing any suitable emulsifier.

In an exemplary embodiment, L-Values of a Visible Residue Index are used to indicate the amount of visibly perceivable color residue that is deposited from applying the antiperspirant products. In this exemplary embodiment, the antiperspirant product has an L-Value of from about 4.5 to about 6.5 indicating a relatively low amount of visibly perceivable color residue being deposited from about a 1 g application. In this example, the Visible Residue Index was measured using the following procedure: a black felt piece of about 10 cm by about 30 cm was immobilized on a flat surface, the dome of the antiperspirant stick product was cut off, the base of the antiperspirant stick product was taped to the bottom of the 250 mL beaker, the antiperspirant stick product and beaker were weighed, a 1 kg weight was placed into the beaker, the antiperspirant stick product was then placed on the black felt, the antiperspirant stick product was then moved slowly across the black felt repeatedly over an area of about 5 cm to about 20 cm at a fixed rate until about 1 g of product had been evenly applied to the felt. A Spectrum DataColor 600 chromameter, which is manufactured by Datacolor located in Lawrenceville, N.J., was used to measure the L-values of the sample 3 times using the black felt as a background, where the L-values were averaged. Without being limited by theory, it is believed that the unique combination of cetyl PEG/PPG-10/1 dimethicone, high MW polyethylene and low MW synthetic wax with substantially no stearyl alcohol in the oil phase results in the antiperspirant product having a relatively low L-Value because the antiperspirant product deposits less color residue which is further masked to minimize its visible effects.

The oil phase further comprises at least one hydrophobic carrier. An example of suitable hydrophobic carriers includes liquid siloxanes and particularly volatile polyorganosiloxanes, that is, liquid materials having a measurable vapor pressure at ambient conditions. The polyorganosiloxanes can be linear or cyclic or mixtures thereof Preferred siloxanes include cyclohexasiloxane and cyclomethicones, such as cyclotetramethicone, cyclopentamethicone, and cyclohexamethicone, and mixtures thereof. The carrier also may comprise, additionally or alternatively, nonvolatile silicones such as dimethicone and dimethicone copolyols. Examples of suitable dimethicone and dimethicone copolyols include polyalkyl siloxanes, polyalkylaryl siloxanes, and polyether siloxane copolymers. In an exemplary embodiment, the oil phase comprises the hydrophobic carrier in an amount of about 2 to about 14 wt. % of the antiperspirant product.

The oil phase may also comprise a high R.I. hydrophobic compound. The high R.I. hydrophobic compound preferably also helps to minimize and/or prevents the visibly perceivable white color residue on the skin by further masking the antiperspirant metallic salt that stays upon the skin upon evaporation of the carrier(s). Examples of high R.I. hydrophobic compounds for use in the antiperspirant products include $C_{12}$-$C_{15}$ alkyl benzoate, such as Finsolv TN® available from Innospec of the United Kingdom, PPG-14 butyl ether, and phenyl dimethicone. In a preferred embodiment, the oil phase comprises $C_{12}$-$C_{15}$ alkyl benzoate and, in a more preferred embodiment, the oil phase comprises $C_{12}$-$C_{15}$ alkyl benzoate in an amount of about 4 to about 11 wt. % of the total antiperspirant product.

In addition to the ingredients identified above, the antiperspirant product may comprise additives, such as those used in conventional antiperspirants. These additives include, but are not limited to, fragrances, including encapsulated fragrances, dyes, pigments, preservatives, antioxidants, moisturizers, and the like. These optional ingredients can be included in the antiperspirant product in an amount of 0 to about 20 wt. %.

Referring to FIG. 1, a schematic illustration of an emulsion processing system 10 for making an antiperspirant product in accordance with an exemplary embodiment is provided. As illustrated, the system 10 comprises a first vessel 12, a second vessel 14 and a third vessel 16. The inventors have found that by controlling various processing conditions in the first, second and third vessels 12, 14 and 16, both harder stick antiperspirant products with lower payout and softer stick antiperspirant products with higher payout in accordance with various embodiments described herein can be produced. In an exemplary embodiment, various ingredients of the water phase including water and an active antiperspirant compound are combined in the first vessel 12 and are heated and mixed to the first temperature. In one example, the various ingredients of the water phase are heated to a first temperature of from about 80 to about 90° C. and are mixed with a mixer blade 18 rotating at about 150 to about 250 revolutions per minute (RPM), and more preferably, at about 200 RPM to form a precursor harder stick and lower payout water phase. In another example, the various ingredients of the water phase are heated to the first temperature of from about 70 to about 79° C. and are mixed with the mixer blade 18 rotating at about 150 to about 250 RPM, and more preferably, at about 200 RPM to form a precursor softer stick and higher payout water phase.

In an exemplary embodiment, various ingredients of the oil phase including a hydrophobic carrier, a structurant, and cetyl PEG/PPG-10/1 dimethicone are combined in the second vessel 14 and are heated and mixed to a second temperature. In one example, the various ingredients of the oil phase are heated to the second temperature of from about 90 to about 95° C. and are mixed with a mixer blade 20 rotating at about 150 to about 250 RPM, and more preferably, at about 200 RPM to melt the structurant and to form the oil phase. Mixing of the oil phase is continued while the oil phase is then cooled to a third temperature in the vessel 14. In one example, the oil phase is cooled to the third temperature of from about 80 to about 90° C. to form a precursor harder stick and lower payout oil phase. In another example, the oil phase is cooled to the third temperature of from about 70 to about 79° C. to form a precursor softer stick and higher payout oil phase.

In an exemplary embodiment, the cooled oil phase is fluidly communicated to the third vessel 16 via line 22 and pump 24. Preferably, substantially all of the oil phase from the second vessel 14 is transferred to the third vessel 16. In the example, where the cooled oil phase is the precursor harder stick and lower payout oil phase, the oil phase in the third vessel 16 is preferably maintained at a temperature of from about 80 to about 90° C. and mixed with a mixer blade 24 at about 150 to about 250 RPM, and more preferably, at about 200 RPM. Alternatively, in the example where the cooled oil phase is the precursor softer stick and higher payout oil phase, the oil phase in the third vessel 16 is preferably maintained at a temperature of from about 70 to about 79° C. and mixed with the mixer blade 24 at about 150 to about 250 RPM, and more preferably, at about 200 RPM.

The water phase is gradually added to the oil phase in the third vessel 16 via line 26 and pump 28 to form an antiperspirant emulsion where the water phase is present in an amount of from about 54 to about 89 wt. % and the oil phase is present in an amount of from about 11 to about 46 wt. % of the antiperspirant emulsion. Alternatively, the second vessel 14 may be used functionally as the third vessel 16 for the gradually adding the water phase to the oil phase to form the antiperspirant emulsion without fluidly communicating the cooled oil phase to the third vessel 16. In an exemplary embodiment, the water phase is gradually added to the oil phase at a transfer rate of about 100 to about 250 mL per minute. The inventors have found that this transfer rate is relatively independent of the batch sizes of the water and oil phases, and further, this relatively slow transfer rate facilitates the formation of an emulsion having very fine water phase droplets suspended in the oil phase for improved overall antiperspirant properties. In the example, where the water and oil phases are the precursor harder stick and lower payout water and oil phases respectively, the temperature of the oil and water phases in the third vessel 16 are maintained at about 80 to about 90° C. Further, the oil and water phases are mixed with the mixer blade 24 at about 150 to about 250 RPM when the water phase is initially added to the oil phase, and then the rotational speed of the mixer blade 24 is gradually increased to be about 500 to about 600 RPM near the completion of adding the water phase to the oil phase. In the example, where the water and oil phases are the precursor softer stick and higher payout water and oil phases respectively, the temperature of the oil and water phases in the third vessel 16 are maintained at about 70 to about 79° C. Moreover, the oil and water phases are mixed with the mixer blade 24 at about 150 to about 250 RPM when the water phase is initially added to the oil phase, and then the rotational speed of the mixer blade 24 is gradually increased to be about 300 to about 400 RPM near the completion of adding the water phase to the oil phase.

In an exemplary embodiment, a hold period after the water phase has been added to the oil phase is conducted where the temperature and mixing conditions are maintained in the third vessel 16 for at least 10 minutes. Any additional ingredients, such as fragrance, can then be added to the antiperspirant emulsion where the holding period is further extended for at least another 5 minutes. The resulting liquid antiperspirant product is fluidly communicated from the third vessel 16 via line 29 and deposited into an appropriate container 30 by any suitable means known to those skilled in the art, such as, for example, via molding or pouring the liquid antiperspirant product, which is then solidified by cooling. Depending upon the processing conditions used to form the antiperspirant product as discussed in the foregoing paragraphs, the antiperspirant product will have either a relatively hard stick with low payout or a relatively soft stick with high payout.

The following is an exemplary embodiment of an antiperspirant product, with each of the components set forth in weight percent of the antiperspirant product. The example is provided for illustration purposes only and is not meant to limit the various embodiments of the antiperspirant product in any way.

EXAMPLE

| Water Phase | | Oil Phase | |
|---|---|---|---|
| Component | wt. % | Component | wt. % |
| Aluminum Zirconium Octachlorohydrex GLY | 12-20 | C12-C15 Alkyl Benzoate | 4-11 |
| | | Polyethylene | 4-12 |
| Propylene glycol | 10-15 | Cetyl PEG/PPG-10/1 dimethicone | 1-3 |
| Calcium Chloride | 2-4 | | |
| Water | 30-50 | Synthetic wax | 0-3 |
| | | Cyclohexasiloxane | 2-14 |
| Total Water Phase | 54-89 | Total Oil Phase | 11-46 |
| | | Fragrance | 0-3 |
| | | Total | 100% |

In the above example, the formulation set forth is suitable for making both harder stick and lower payout antiperspirant products and softer stick and higher payout antiperspirant products. The inventors have found that by following the various embodiments described in the foregoing paragraphs in reference to FIG. 1, the example formulation can be used to produce antiperspirant products with different stick hardnesses and different payouts that deposit relatively low amounts of visibly perceivable color residue and which exhibit antiperspirant efficacy with the feel of deodorants.

Accordingly, antiperspirant products with antiperspirant efficacy that exhibit improved skin feel and processes for making such antiperspirant products have been provided. The various embodiments of the antiperspirant product comprise cetyl PEG/PPG-10/1 dimethicone as an emulsifier. The use of cetyl PEG/PPG-10/1 dimethicone as an emulsifier in an antiperspirant product causes the antiperspirant product to glide onto the skin with less friction, that is, in a smoother manner, than conventional antiperspirants while still maintaining a solid consistency for easy application. The various embodiments of the antiperspirant emulsion products also comprise a unique combination of structurants that result in less color residue on the skin. Further, the various embodiments contemplated herein relate to unique processes for making the antiperspirant emulsion products that result in either relatively hard or soft antiperspirant sticks with corresponding relatively low or high payouts.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for making an antiperspirant emulsion product, the process comprising the steps of:
   heating and mixing water and an active antiperspirant compound to about 80 to about 90° C. to form a precursor harder stick and lower payout water phase or heating to about 70 to about 79° C. and mixing water and the active antiperspirant compound to form a precursor softer stick and higher payout water phase;
   heating and mixing a hydrophobic carrier, a structurant, and cetyl PEG/PPG-10/1 dimethicone to about 90 to about 95° C. to form an oil phase and cooling the oil phase to about 80 to about 90° C. to form a precursor harder stick and lower payout oil phase or cooling the oil phase to about 70 to about 79° C. to form a precursor softer stick and higher payout oil phase; and
   combining the precursor harder stick and lower payout water phase with the precursor harder stick and lower payout oil phase to form a harder stick and lower payout antiperspirant emulsion product or combining the precursor softer stick and higher payout water phase with the softer stick and higher payout oil phase to form a softer stick and higher payout antiperspirant emulsion product.

2. The process according to claim 1, wherein the step of heating and mixing the water and the active antiperspirant compound comprises mixing the water and the active antiperspirant compound with a mixer blade rotating at about 150 to about 250 RPM.

3. The process according to claim 1, wherein the step of heating and mixing the hydrophobic carrier, the structurant, and the cetyl PEG/PPG-10/1 dimethicone comprises mixing the hydrophobic carrier, the structurant, and the cetyl PEG/PPG-10/1 dimethicone with a mixer blade rotating at about 150 to about 250 RPM.

4. The process according to claim 1, wherein the step of cooling and mixing the oil phase comprises mixing the oil phase with a mixer blade rotating at about 150 to about 250 RPM.

5. The process according to claim 1, wherein the step of gradually adding the water phase comprises gradually adding the water phase to the oil phase at a transfer rate of from about 100 to about 250 mL/min.

6. The process according to claim 1, wherein the step of heating and mixing the hydrophobic carrier comprises heating and mixing the hydrophobic carrier, the structurant comprising high MW polyethylene, and the cetyl PEG/PPG-10/1 dimethicone.

7. The process according to claim 1, further comprising the step of mixing the water phase and the oil phase during the step of gradually adding the water phase to the oil phase.

8. The process according to claim 7, wherein the step of mixing the water phase and the oil phase comprises mixing the water phase and the oil phase with a mixer blade rotating at about 150 to about 250 RPM during an initial period of the step of gradually adding the water phase, and then gradually increasing a rotational speed of the mixer blade such that the mixer blade is rotating at about 500 to about 600 RPM during a final period of the step of gradually adding the water phase.

9. The process according to claim 7, wherein the step of mixing the water phase and the oil phase comprises mixing the water phase and the oil phase with a mixer blade rotating at about 150 to about 250 RPM during an initial period of the step of gradually adding the water phase, and then gradually increasing a rotational speed of the mixer blade such that the mixer blade is rotating at about 300 to about 400 RPM during a final period of the step of gradually adding the water phase.

10. The process according to claim 7, wherein the step of cooling and mixing the oil phase comprises cooling the oil phase to the third temperature that is about the same as the first temperature, and the process further comprising the step of maintaining the water and oil phases at about the third temperature during the steps of gradually adding the water phase to the oil phase and mixing the water phase and the oil phase.

11. The process according to claim 10, wherein the steps of mixing the water phase and the oil phase and maintaining the water and oil phases at about the third temperature continue for a hold period of at least about 10 minutes after the completion of the step of gradually adding the water phase to the oil phase, and wherein the step of mixing the water phase and the oil phase further comprises mixing the antiperspirant emulsion during the hold period.

12. The process according to claim 11, further comprising the steps of:
   mixing a fragrance into the antiperspirant emulsion after the hold period while continuing to maintain the antiperspirant emulsion at the third temperature for a mixing period of at least about 5 minutes; and
   depositing the antiperspirant emulsion into a container and allowing the antiperspirant emulsion to solidify.

* * * * *